US009538761B2

(12) United States Patent
Shah

(10) Patent No.: US 9,538,761 B2
(45) Date of Patent: Jan. 10, 2017

(54) PESTICIDAL COMPOSITION COMPRISING SULPHUR, A FUNGICIDE AND AN AGROCHEMICAL EXCIPIENT

(76) Inventor: Deepak Pranjivandas Shah, Mumbai (IN)

(*) Notice: Subject to any disclaimer, the term of this patent is extended or adjusted under 35 U.S.C. 154(b) by 0 days.

(21) Appl. No.: 13/981,611

(22) PCT Filed: Jan. 30, 2012

(86) PCT No.: PCT/IN2012/000067
§ 371 (c)(1),
(2), (4) Date: Jul. 25, 2013

(87) PCT Pub. No.: WO2012/101660
PCT Pub. Date: Aug. 2, 2012

(65) Prior Publication Data
US 2013/0309327 A1    Nov. 21, 2013

(30) Foreign Application Priority Data
Jan. 28, 2011  (IN) .......................... 252/MUM/2011

(51) Int. Cl.
| | | |
|---|---|---|
| *A01N 59/02* | (2006.01) | |
| *A01N 35/04* | (2006.01) | |
| *A01N 37/24* | (2006.01) | |
| *A01N 37/34* | (2006.01) | |
| *A01N 37/50* | (2006.01) | |
| *A01N 43/16* | (2006.01) | |
| *A01N 43/30* | (2006.01) | |
| *A01N 43/50* | (2006.01) | |
| *A01N 43/54* | (2006.01) | |
| *A01N 43/653* | (2006.01) | |
| *A01N 47/24* | (2006.01) | |
| *A01N 47/32* | (2006.01) | |
| *A01N 47/34* | (2006.01) | |
| *A01N 47/38* | (2006.01) | |

(52) U.S. Cl.
CPC .............. *A01N 59/02* (2013.01); *A01N 35/04* (2013.01); *A01N 37/24* (2013.01); *A01N 37/34* (2013.01); *A01N 37/50* (2013.01); *A01N 43/16* (2013.01); *A01N 43/30* (2013.01); *A01N 43/50* (2013.01); *A01N 43/54* (2013.01); *A01N 43/653* (2013.01); *A01N 47/24* (2013.01); *A01N 47/32* (2013.01); *A01N 47/34* (2013.01); *A01N 47/38* (2013.01)

(58) Field of Classification Search
CPC .... A01N 2300/00; A01N 59/02; A01N 51/00; A01N 53/00
See application file for complete search history.

(56) References Cited

U.S. PATENT DOCUMENTS

| | | | |
|---|---|---|---|
| 6,380,135 B1* | 4/2002 | Reuter et al. ................ | 504/366 |
| 7,635,404 B1 | 12/2009 | Devic et al. | |
| 2002/0099062 A1* | 7/2002 | Cotter .................... | A01N 35/04 514/269 |
| 2007/0123541 A1* | 5/2007 | Grosjean-Cournoyer et al. ........................ | 514/254.07 |
| 2010/0122379 A1* | 5/2010 | Dieckmann et al. ......... | 800/295 |

FOREIGN PATENT DOCUMENTS

| | | | |
|---|---|---|---|
| CN | 1260957 A | | 7/2000 |
| CN | 101366378 A | * | 2/2009 |
| CN | 101720756 A | | 6/2010 |
| CN | 101940120 A | | 1/2011 |
| EP | 1023834 B1 | | 8/2000 |
| FR | 2585539 A1 | | 2/1987 |
| JP | 04257502 A | | 9/1992 |
| WO | 02067679 A1 | | 9/2002 |
| WO | 2010108973 A2 | | 9/2010 |

OTHER PUBLICATIONS

Ciobanu R. I. et. al, "Effect of Pesticides on Cellular Ultrastructure of Triticum aestivum L.", Stiinte, Agricole si Silvice, 1990, 23, 273-278 & CAPLUS Database AN 117:42584; Abstract.
Solarska E. & Pietrzak T, "The Efficacy of Several Fungicides in the Hop False Downy Mildew Control", Pamietnik Pulawski, 1990, 95, 71-82 & CAPLUS Database AN 116:230099; Abstract.
Vilau F. et. al, "Control of Cereal Diseases with Metozir and Metozir S", Stiinte Agricole si Silvice, 1990,23, 189-293 & CAPLUS Databse 116:230096; Abstract.
Ene L. et. al, "Effect of Ziram on the Protein Content of Wheat Kernels", Stiinte Agricole si Silvice, 1990,23,285-293 & CAPLUS Databse AN 116:2096 18, Abstract.
Brignani N. F. et. al, "Efficacy of Some Fungicides for Control of Early Blight (*Alternaria solani*) of Potato", Summa Phytopathologica, 1990, 16, 263-268 & CAPLUS Database AN 115:152957, Abstract.
Bobes I. et. al, "Control of Barley Powdery Mildew by Chemical Treatments Applied During Vegetation Period", Buletinul Institutului Agronomic Cluj-Napoca, Seria Agriculture, 1979,33,83-86 & CAPLUS Database AN 95: 17 13 Abstract.
Pauwels W. J & Schauer R. L, "Control of Cereal Diseases with Chlorothalonil and Chlorothalonil + Maneb + Sulfur", Mededelingen van de Faculteit Landbouwwetenschappen, Universiteit Gent, 1976,41,687-692 & CAPLUS Database AN 86: 15 1352; Abstract.
Kingsland G. C. & Sitterly W. R, "Studies on Fungicides for Control of Corynespora Cassiicola Leafspot of Tomatoes in the Republic of Seychelles", Trop. Pest Manage., 1986,32,31-34, Abstract, col. 2, table 1.

(Continued)

*Primary Examiner* — Kyle Purdy
(74) *Attorney, Agent, or Firm* — Wiley Rein LLP

(57) ABSTRACT

A pesticidal composition comprising sulphur, a fungicide selected from the group consisting of cymoxanil, fenhexamid, fenamidone, cyazofamid, chlorothalonil, kresoxim methyl, azoxystrobin, trifloxystrobin, pyraclostrobin, iprodione, validamycin, kasugamycin, cyprodinil, pencycuron, hexaconazole, prochloraz, epoxiconazole, prothioconaozole, trifloxystrobin, thiophanate methyl, spiroxamine, metrafenone or their salts thereof and at least one agrochemically acceptable excipient.

11 Claims, No Drawings

(56) References Cited

OTHER PUBLICATIONS

Vulsteke G & Meeus P, "Nieuwe Ziektebestrijdingsmiddelen Bij Schorseneer", Med. Fac. Landbouww. Rijksuniv. Gent, 198 1,46,1003-1015, Abstract, tables 1-11.
Poulsen M. E. et. al, "Influence of Different Disease Control Pesticide Strategies on Multiple Pesticide Residue Levels in Apple", J. Hortic. Sci. Biotech., 2009, 58-61, Abstract, tables 1-11.
Matheron M. E & Porchas M, "Comparative Performance and Preservation of Chemical Management Tools for Powdery Mildew on Muskmelon", Acta Horticulturae, 2007, 73 1, 357-361 Abstract, p. 358, table 1.
De Kock P. J & Holz G, "Application of Fungicides Against Postharvest Botrytis cinerea Bunch Rot of Table Grapes in the Western Cape", S. Afr. J. Enol. Vitic., 1994, 15,33-40; Abstract, cols. 2-3,6, tables 3-4.
Tomlin C. D. S. (Ed.), "The Pesticide Manual", 15th ed., 2009, BCPC:Hampshire, UK; Entries 52, 153, 198, 215, 223, 322, 350, 358, 460, 498, 515, 517, 592, 659, 699, 725, 730, 788, 801, 883, 852, 897.

* cited by examiner

PESTICIDAL COMPOSITION COMPRISING SULPHUR, A FUNGICIDE AND AN AGROCHEMICAL EXCIPIENT

BACKGROUND OF THE INVENTION

Field of the Invention

The present invention relates to a pesticidal composition comprising an effective amount of sulphur; an effective amount of at least one fungicide or its salt, and at least one agrochemically acceptable excipient. The invention further relates to a method of application of the pesticidal composition to crops.

Description of the Related Art

The role of elemental sulphur as a pesticide has been known for a long time. The role of sulphur in controlling, inhibiting and eradicating the growth of fungi such as mildews is well known. Sulphur is mostly available in its elemental form and different formulations such as granules, pellets, powders, etc. are known for providing sulphur in a form for use as a fertilizer or pesticide. Sulphur formulations used alone are good to moderately effective against powdery mildew and other fungal diseases. Sulphur not only works as a fungicide, for example on powdery mildew or grey mildew but is also used as a supplementary plant nutrient.

Further demands on fungicidal compounds include reduced phytotoxicity, reduced dosage, substantial broadening of spectrum and increased safety, to name a few.

The biological properties of known compounds are not entirely satisfactory in the areas of plant disease control, environmental and worker exposure, for example in particular, it has been observed that pathogens become, resistant to pesticides which are at times administered in higher dosages to achieve the desired control, thereby leading to soil toxicity and other environmental hazards, besides higher costs.

Hence, there is a need to develop a composition which addresses the problems of resistance and soil toxicity and also is used at reduced dosages, controls environmental damage, offers broader crop protection spectrum, improved and healthy foliage, improved rainfastness, improves crop yield, saves labour, better grain quality and control against various plant pathogens and various classes of fungi, improves plant growth and is yet cost-effective to the end user.

SUMMARY OF THE INVENTION

It has now been discovered that a pesticidal composition comprising sulphur, a fungicide selected from the group consisting of fenhexamid, fenamidone, cyazofamid, chlorothalonil, kresoxim methyl, azoxystrobin, pyraclostrobin, iprodione, validamycin, kasugamycin, cyprodinil, pencycuron, hexaconazole, prochloraz, epoxiconazole, prothioconaozole, trifloxystrobin, thiophanate methyl, spiroxamine, metrafenone or salts thereof and at least one agrochemically acceptable excipient, has unexpectedly high activities in the control of various fungi such as powdery mildew, downy mildew, rusts, blight, etc.

Surprisingly it has also been further discovered by the inventors of the application that a pesticidal composition comprising sulphur in the range from 25% to 70%, cymoxanil or salts thereof in the range from 25% to 70% and at least one agrochemically acceptable excipient demonstrates excellent control over certain diseases for eg late blight.

The pesticidal compositions offers a broad spectrum of protection, addresses the concerns of resistance, improves foliage, improves rainfastness and in various instances, improves crop yield and grain quality. The compositions disclosed herein, also serve as an intervention application between very specific actives, which alone are likely to lead to resistance in areas of epidemic and high frequency of pesticidal application. In certain cases, the compositions also addresses the need of pre-harvest and post-harvest application that further helps preserve the shelf life of fruits, vegetables, etc.

Quite advantageously, in certain cases, the compositions can be applied as a foliar spray or to the soil, through broadcasting or through drip or trickle irrigation. The latter case of drip or trickle irrigation further optimizes farming practices, which are greatly challenged by an ever-increasing labour and water shortage. In some cases, it has been observed, that the compositions at very low concentrations of the active ingredients can be effectively applied, thereby reducing the burden on the environment. In certain cases, it has also been noted that the compositions at lower rates of the active ingredients in combination together provided a longer duration of control of the disease incidence.

DETAILED DESCRIPTION

In describing the embodiments of the invention, specific terminology is resorted for the sake of clarity. However, it is not intended that the invention be limited to the specific terms so selected and it is to be understood that each specific term includes all technical equivalents that operate in a similar manner to accomplish a similar purpose.

The present invention relates to a pesticidal composition comprising an effective amount of a sulphur, an effective amount of at least one fungicide selected from the group consisting of fenhexamid, fenamidone, cyazofamid, chlorothalonil, kresoxim methyl, azoxystrobin, pyraclostrobin, iprodione, validamycin, kasugamycin, cyprodinil, pencycuron, hexaconazole, prochloraz, epoxiconazole, prothioconaozole, trifloxystrobin, thiophanate methyl, spiroxamine, metrafenone or salts thereof and at least one agrochemically acceptable excipient.

According to an embodiment, sulphur is present in a range from 7.5% to 80% of the total weight of the composition. According to an embodiment, the fungicide is present in a range from 1% to 70% of the total weight of the composition.

The pesticidal composition can be in a solid form or a liquid form. For e.g., the pesticidal composition may be in the form of emulsion concentrates, wettable powders, suspension concentrates, suspo emulsions, microemulsions, capsulated suspensions, water dispersible granules, pellets, seed dressings or emulsions for seed treatment, broadcast granules, gels, emulsions in water, oil dispersions, etc.

Preferably, the pesticidal composition is in the form of water dispersible granules. When the composition is in the form of water dispersible granules, usually sulphur is present in the range from 15% to 80% and the fungicide is usually present in the range from 1.5% to 70% of the total composition.

Preferably, the pesticidal composition is in the form of suspension concentrates. When the composition is in the form suspension concentrates, usually sulphur is present in the range from 7.5% to 70% and the fungicide is usually present in the range from 1% to 35% of the total composition.

Water dispersible granules can be defined as a pesticide formulation consisting of granules to be applied after disintegration and dispersion in water. As described herein, "WG" or "WDG" refer to water dispersible granules.

Suspension concentrate can be defined as a stable suspension of solid pesticides in a fluid usually intended for dilution with water before use. As described herein, "SC" refers to suspension concentrates.

As defined herein, WP refers to a wettable powder, which can be a powder formulation to be applied as a suspension after dispersion in water. As defined herein, EC refers to an emulsifiable concentrate, which can be a liquid homogenous formulation to be applied as an emulsion after dilution in water. As defined herein, SE refers to suspo-emulsion which is a formulation containing both solid and liquid (or low melting point solid+solvent) active ingredients dispersed in an aqueous phase. As described herein, ZC refers to a stable suspension of capsules and active ingredient, in fluid, normally intended for dilution with water before use.

As used herein, the abbreviation 'DAS' refers to days after spraying. As described herein, the abbreviation "DAT" refers to Days after Transplanting. As described herein, the abbreviation "DAP" refers to Days after Planting.

According to an embodiment, the composition comprises sulphur in the range from 17.5% to 60% and fenhexamid in the range from 12.5% to 65% of the total weight of the composition. According to another embodiment, sulphur is in the range from 20% to 60% and fenhexamid is in the range from 25% to 65% of the total weight of the composition in the form of water dispersible granules. According to another embodiment, sulphur is in the range from 17.5% to 70% and fenhexamid is in the range from 12.5% to 25% of the total weight of the composition in the form of suspension concentrate.

According to an embodiment, sulphur is in the range from 25% to 80% and fenamidone is in the range from 3% to 20% of the total weight of the composition. According to another embodiment, sulphur is in the range from 50% to 80% and fenamidone is in the range from 4% to 20% of the total weight of the composition in the form of water dispersible granules. According to another embodiment, sulphur is in the range from 25% to 70% and fenamidone is in the range from 3% to 15% of the total weight of the composition in the form of suspension concentrate.

According to an embodiment, sulphur is in the range from 25% to 75% and cyazofamid is in the range from 2.25% to 40% of the total weight of the composition. According to another embodiment, sulphur is in the range from 40% to 75% and cyazofamid is in the range from 10% to 40% of the total weight of the composition in the form of water dispersible granules. According to another embodiment, sulphur is in the range from 25% to 70% and cyazofamid is in the range from 2.25% to 20% of the total weight of the composition in the form of suspension concentrate.

According to an embodiment, sulphur is in the range from 25% to 70% and chlorothalonil is in the range from 7.5% to 50% of the total weight of the composition. According to another embodiment, sulphur is in the range from 35% to 70% and chlorothalonil is in the range from 15% to 50% of the total weight of the composition in the form of water dispersible granules. According to another embodiment, sulphur is in the range from 25% to 70% and chlorothalonil is in the range from 7.5% to 25% of the total weight of the composition in the form of suspension concentrate.

According to an embodiment, sulphur is in the range from 25% to 70% and kresoxim-methyl is in the range from 11% to 40% of the total weight of the composition. According to another embodiment, sulphur is in the range from 40% to 70% and kresoxim-methyl is in the range from 10% to 40% of the total weight of the composition in the form of water dispersible granules. According to another embodiment, sulphur is in the range from 25% to 60% and kresoxim-methyl is in the range from 11% to 20% of the total weight of the composition in the form of suspension concentrate.

According to an embodiment, sulphur is in the range from 25% to 80% and azoxystrobin is in the range from 3% to 20% of the total weight of the composition. According to another embodiment, sulphur is in the range from 50% to 80% and azoxystrobin is in the range from 5% to 20% of the total weight of the composition in the form of water dispersible granules. According to another embodiment, sulphur is in the range from 25% to 70% and azoxystrobin is in the range from 3% to 20% of the total weight of the composition in the form of suspension concentrate.

According to an embodiment, sulphur is in the range from 30% to 75% and pyraclostrobin is in the range from 3.5% to 15% of the total weight of the composition. According to another embodiment, sulphur is in the range from 60% to 75% and pyraclostrobin is in the range from 7% to 15% of the total weight of the composition in the form of water dispersible granules. According to another embodiment, sulphur is in the range from 30% to 70% and pyraclostrobin is in the range from 3.5% to 10% of the total weight of the composition in the form of suspension concentrate.

According to an embodiment, sulphur is in the range from 17.5% to 55% and iprodione is in the range from 15% to 60% of the total weight of the composition. According to another embodiment, sulphur is in the range from 25% to 55% and iprodione is in the range from 30% to 60% of the total weight of the composition in the form of water dispersible granules. According to another embodiment, sulphur is in the range from 17.5% to 65% and iprodione is in the range from 15% to 25% of the total weight of the composition in the form of suspension concentrate.

According to an embodiment, sulphur is in the range from 25% to 80% and validamycin is in the range from 1.5% to 10% of the total weight of the composition. According to another embodiment, sulphur is in the range from 50% to 80% and validamycin is in the range from 3% to 10% of the total weight of the composition in the form of water dispersible granules. According to another embodiment, sulphur is in the range from 35% to 70% and validamycin is in the range from 1.5% to 10% of the total weight of the composition in the form of suspension concentrate.

According to an embodiment, sulphur is in the range from 25% to 80% and kasugamycin is in the range from 1.5% to 10% of the total weight of the composition. According to another embodiment, sulphur is in the range from 50% to 80% and kasugamycin is in the range from 1.5% to 10% of the total weight of the composition in the form of water dispersible granules. According to another embodiment, sulphur is in the range from 35% to 70% and kasugamycin is in the range from 1.5% to 10% of the total weight of the composition in the form of suspension concentrate.

According to an embodiment, sulphur is in the range from 25% to 70% and cyprodinil is in the range from 5% to 30% of the total weight of the composition. According to another embodiment, sulphur is in the range from 50% to 70% and cyprodinil is in the range from 10% to 30% of the total weight of the composition in the form of water dispersible granules. According to another embodiment, sulphur is in the range from 25% to 70% and cyprodinil is in the range from 5% to 20% of the total weight of the composition in the form of suspension concentrate.

According to an embodiment, sulphur is in the range from 25% to 70% and pencycuron is in the range from 5% to 30% of the total weight of the composition. According to another embodiment, sulphur is in the range from 50% to 70% and pencycuron is in the range from 6% to 30% of the total weight of the composition in the form of water dispersible granules. According to another embodiment, sulphur is in the range from 25% to 70% and pencycuron is in the range from 5% to 15% of the total weight of the composition in the form of suspension concentrate.

According to an embodiment, sulphur is in the range from 30% to 80% and hexaconazole is in the range from 1.5% to 8% of the total weight of the composition. According to another embodiment, sulphur is in the range from 60% to 80% and hexaconazole is in the range from 2% to 8% of the total weight of the composition in the form of water dispersible granules. According to another embodiment, sulphur is in the range from 32% to 70% and hexaconazole is in the range from 1.5% to 8% of the total weight of the composition in the form of suspension concentrate.

According to an embodiment, sulphur is in the range from 20% to 70% and prochloraz is in the range from 12.5% to 60% of the total weight of the composition. According to another embodiment, sulphur is in the range from 25% to 70% and prochloraz is in the range from 10% to 60% of the total weight of the composition in the form of water dispersible granules. According to another embodiment, sulphur is in the range from 20% to 60% and prochloraz is in the range from 12.5% to 30% of the total weight of the composition in the form of suspension concentrate.

According to an embodiment, sulphur is in the range from 30% to 80% and epoxiconazole is in the range from 1.5% to 20% of the total weight of the composition. According to another embodiment, sulphur is in the range from 60% to 80% and epoxiconazole is in the range from 3% to 20% of the total weight of the composition in the form of water dispersible granules. According to another embodiment, sulphur is in the range from 30% to 70% and epoxiconazole is in the range from 1.5% to 10% of the total weight of the composition in the form of suspension concentrate.

According to an embodiment, sulphur is in the range from 20% to 70% and prothioconazole is in the range from 5% to 60% of the total weight of the composition. According to another embodiment, sulphur is in the range from 25% to 70% and prothioconazole is in the range from 5% to 60% of the total weight of the composition in the form of water dispersible granules. According to another embodiment, sulphur is in the range from 20% to 70% and prothioconazole is in the range from 5% to 30% of the total weight of the composition in the form of suspension concentrate.

According to an embodiment, sulphur is in the range from 7.5% to 60% and thiophanate methyl is in the range from 12.5% to 70% of the total weight of the composition. According to an embodiment, sulphur is in the range from 15% to 60% and thiophanate methyl is in the range from 25% to 70% of the total weight of the composition in the form of water dispersible granules. According to an embodiment, sulphur is in the range from 7.5% to 60% and thiophanate methyl is in the range from 12.5% to 35% of the total weight of the composition in the form of suspension concentrate.

According to an embodiment, sulphur is in the range from 20% to 70% and trifloxystrobin is in the range from 1% to 40% of the total weight of the composition. According to an embodiment, sulphur is in the range from 40% to 70% and trifloxystrobin is in the range from 2% to 40% of the total weight of the composition in the form of water dispersible granules. According to another embodiment, sulphur is in the range from 20% to 70% and trifloxystrobin is in the range from 1% to 20% of the total weight of the composition in the form of suspension concentrate.

According to an embodiment, sulphur is in the range from 11% to 80% and spiroxamine is in the range from 6% to 35% of the total weight of the composition. According to an embodiment, sulphur is in the range from 40% to 80% and spiroxamine is in the range from 6% to 35% of the total weight of the composition in the form of wettable powder. According to another embodiment, sulphur is in the range from 11% to 40% and spiroxamine is in the range from 6% to 20% of the total weight of the composition in the form of suspo emulsion. According to an embodiment, the composition comprising sulphur and spiroxamine can be in the form of a ZC.

According to an embodiment, sulphur is in the range from 25% to 70% and metrafenone is in the range from 5% to 30% of the total weight of the composition. According to an embodiment, sulphur is in the range from 50% to 70% and metrafenone is in the range from 10% to 30% of the total weight of the composition in the form of water dispersible granules. According to another embodiment, sulphur is in the range from 25% to 70% and metrafenone is in the range from 5% to 15% of the total weight of the composition in the form of suspension concentrate.

The invention further relates to a pesticidal composition comprising sulphur in the range from 25% to 70%, cymoxanil or salts thereof in the range from 7.5% to 30% of the total weight of the composition and at least one agrochemically acceptable excipient. According to another embodiment, sulphur is in the range from 50% to 70% and cymoxanil is in the range from 15% to 30% of the total weight of the composition in the form of water dispersible granules.

According to another embodiment, sulphur is in the range from 25% to 70% and cymoxanil is in the range from 7.5% to 15% of the total weight of the composition in the form of suspension concentrate.

According to yet another embodiment, the at least one agrochemically acceptable excipient can comprise wetting agents, dispersing agents, emulsifiers, binding agents, sticking agents, fillers, diluents, solvents, coating agents and stabilizers. However, those skilled in the art will appreciate that it is possible to utilize additional agrochemically acceptable excipients without departing from the scope of the present invention. The agrochemically acceptable excipient is in the range from 7% to 70% of the total weight of the composition.

Wetting agents which can be commonly used include sulfosuccinates, naphthalene sulfonates, sulfated esters, phosphate esters, sulfated alcohol and alkyl benzene sulfonates. However, those skilled in the art will appreciate that it is possible to utilize other wetting agents known in the art without departing from the scope of the invention.

Dispersing agents which can be commonly used include polycarboxylates, naphthalene sulfonate condensates, phenol sulfonic acid condensates, lignosulfonates, methyl oleyl taurates and polyvinyl alcohols. However, those skilled in the art will appreciate that it is possible to utilize other dispersing agents known in the art without departing from the scope of the invention.

Emulsifiers can be of the anionic, cationic or non-ionic type. Emulsifiers which do not cause the liquid active substance to solidify are particularly preferred. Some liquid actives are completely miscible in water and may not require an emulsifier. These emulsifiers are usually used in admixture. The emulsifiers which are commonly used include ethoxylated and ethopropoxylated alcohols and nonyl phenols, ethoxylated tristeryl phenol, ethoxylated tristeryl phenol phosphates, ethoxylated and ethopropoxylated castor oil, calcium alkyl benzene sulfonates and proprietary blended emulsifiers. However, those skilled in the art will appreciate that it is possible to utilize other emulsifiers known in the art without departing from the scope of the invention.

Fillers which can be commonly used include diatomaceous earth, kaolin, bentonite, precipitated silica, attapulgite, and perlite. However, those skilled in the art will appreciate that it is possible to utilize other fillers known in the art without departing from the scope of the invention.

Diluents which can be commonly used include one or more of tone calcite, mica, soap powder, dolomite and lactose. However, those skilled in the art will appreciate that it is possible to utilize other diluents known in the art without departing from the scope of the invention.

Solvents which can be commonly used include one or more of N,N-dimethyl decanamide, N-methylpyrrolidone, cyclohexanone, dimethyl formamide, tetrahydrofuran, dimethylsulfoxide, petroleum distillates and chlorobenzenes. However, those skilled in the art will appreciate that it is possible to utilize other solvents known in the art without departing from the scope of the invention.

The compositions comprising sulphur and a fungicide can be prepared by various processes. Water dispersible granule compositions can be made by various processes which include spray drying, fluid bed spray drying, extrusion, pan granulation, etc. One way of making, water dispersible granular compositions which include sulphur and the fungicide involves initially blending required additives such as wetting agents, dispersing agents, emulsifiers, solvents, fillers to obtain an additive mix. The additive mix obtained is dispersed in sufficient quantity of water to form a blend. A requisite amounts of fungicide technical and sulphur technical are slowly added to the blend by high shear mixing. Further agrochemically acceptable excipients such as fillers can be added, if required to form a mixture. The above mixture is wet milled using a bead mill to obtain an average particle size of less than 50 microns, preferably less than 15 microns, preferably 1 to 10 microns to obtain the mill base. The mill base is granulated in an appropriate spray drier or using other drying methods and at a suitable temperature followed by sieving to remove the under-sized and the oversized granules, to obtain a WG formulation comprising sulphur and fungicide in combination.

Alternately stable aqueous suspension concentrates compositions of sulphur and the fungicide may be prepared by blending required additives such as wetting agents, dispersing agents, emulsifiers, fillers to obtain an additive mix. Then a mill base having an average particle size of less than 50 microns, preferably less than 15 microns, preferably 1 to 10 microns is prepared by milling a mixture of requisite amount of the fungicide and sulphur technical in appropriate ratios in the additive mix in required amount of water containing sufficient amount of solvent. Further, sufficient quantity of water with required amount of additives such binding agents and preservative are added to the mill base and mixed thoroughly to get the SC formulations of the desired combination of sulphur and the fungicide.

Alternately, wettable powder compositions of sulphur and solid fungicide can be prepared by blending required additives such as wetting agents, dispersing agents, emulsifiers, fillers to obtain an additive mix. Further essential amount of sulphur and fungicide technical are blended thoroughly with appropriate proportion of the additive mix, carrier and the required amount of filler. The mixture is then micronised using a suitable mill like fluid energy mill, jet mill, pin mill, hammer mill to an average particle size of less than 50 microns, preferably less than 15 microns, preferably 4 to 10 microns to get the WP formulation comprising sulphur and fungicide in combination.

The wettable powder compositions of sulphur and liquid fungicide can be prepared by blending required additives such as wetting agents, dispersing agents, emulsifiers, fillers to obtain an additive mix. An essential quantity of sulphur technical, additive mix and optionally filler are blended together and are then micronised using a suitable mill like fluid energy mill to an average particle size of less than 50 microns, preferably less than 15 microns, preferably 4 to 10 microns to obtain sulphur base. The requisite amount of liquid pesticide is then absorbed on carrier to obtain fungicide base. The proportionate amount of the fungicide base and the sulphur base are blended thoroughly to get the WP fomulation.

Alternately, emulsifiable concentrate (EC) compositions can be prepared by dissolving required quantity of the fungicide in a solvent to obtain a solution. A blend of non ionic and an anionic emulsifier is added to the solution to obtain the EC of the fungicide.

According to an embodiment, the invention relates to a method of application of an effective amount of the pesticidal composition, wherein the composition is applied to crops through foliar spray or soil application or through drip irrigation or trickle irrigation to effectively reach the roots of desired crops.

Through the agrochemical composition it has been observed that the number of applications to control wide range of fungal diseases and infections appearing at the same time is minimized. The composition is highly safe to the user and to the environment. The composition also is cost-effective, as it provides much greater simultaneous control and can be used in a variety of crops with a broader spectrum of protection over an extended period of time as compared to the stand alone applications of pesticides. The composition also exhibits an improved rainfastness and reduced spill off. The crops treated with the composition display an improved foliage and an enhanced yield and an improved grain quality with the presence of sulphur in the composition. In some cases, the crops have a higher percentage of oil and better tolerance to natural abiotic factors. The composition also serves to meet the need of sulphur fertilizer required in the initial stages of plant growth. Lesser applications or treatments of the composition are required while achieving an effective control over a wide range of fungal diseases thereby rendering the composition highly economical to the end user. Also, the compositions serve as an intervention application between very specific actives which alone are likely to lead to resistance in areas of epidemic and high frequency of pesticidal applications, more so where extended disease management programs are to be followed.

EXAMPLES

Example 1

Sulphur 80%+Trifloxystrobin 2.5% WG

Step 1: Preparation of 'Additive Mix'

25 parts of Sodium salt of naphthalene sulfonate condensate (eg. Tamol NN 8906), 25 parts of Sodium salt of phenol sulfonate condensate (eg. Tamol PP), 100 parts of Sodium lignin sulfonate (eg. Reax 100M) and 50 parts of Kaolin (eg. Barden clay) are blended together and used as 'additive mix'.

Step 2: Preparation of Mill Base 15.7 parts of 'additive mix' is first dispersed in 100 parts of water. Added slowly 2.8 parts of Trifloxystrobin technical (95% purity) and 81.5 parts of sulphur technical (99% purity) under high shear mixing. The mixture is wet milled using a bead mill to an average particle size of around 2 microns to get the mill base.

Step 3: Spray Granulation of Mill Base

The above mill base is spray granulated in an appropriate spray drier with an out let temperature around 70 degree C. followed by sieving to remove the under sized and oversized, to get Sulphur 80%+Trifloxystrobin 2.5% WG.

Example 2

Sulphur 50%+Chlorothalonil 30% WG

Mill base prepared by milling a mixture of 32 parts of Chlorothalonil technical (95% purity), 51.5 parts of sulphur technical (99% purity), 16.5 parts of 'additive mix' in 100 parts of water is spray granulated as in Example 1 to get Sulphur 50%+Chlorothalonil 30% WG.

Example 3

Sulphur 65%+Difenoconazole 15% WG

Mill base prepared by milling a mixture of 16 parts of Difenoconazole technical (96% purity), 66.5 parts of sulphur technical (99% purity), 17.5 parts of 'additive mix' in 100 parts of water is spray granulated as in Example 1 to get Sulphur 65%+Difenoconazole 15.0% WG.

Example 4

Sulphur 35%+Kresoxim Methyl 7.5% SC

Mill base, having an average particle size of around 2 microns, is prepared as in Example 1 by milling a mixture of 7.8 parts of Kresoxim methyl (97% purity), 35.5 parts of sulphur technical (99% purity), 10 parts of 'additive mix' in 33.2 parts of water containing 5 parts of propylene glycol. 8.5 parts of 2% dispersion of xanthum gum (eg. Rhodopol) in water containing 0.5% 1,2-Benzisothiazolin-3-one (eg. Proxel) is then added to the mill base and mixed thoroughly to get Sulphur 35%+Kresoxim methyl 7.5% SC.

Efficacy Trials:

The efficacy trials conducted using stand-alone treatments of sulphur and the fungicides were done in accordance with the standard recommended dosages for these active ingredients in India. However, it may be noted that recommended dosages for each active ingredient may vary as per recommendations in a particular country, soil conditions, weather conditions and disease incidence

Example 1

Bioefficacy of Sulphur Plus Fenhexamid

The experiment was laid out with nine treatments and replicated thrice in the Nasik district of Maharashtra state in India by adopting uniform agronomic practices for all the replication and treatments. The treatments were carried out in grapes and included combinations of Fenhexamid with Sulphur in varying concentrations and also included Fenhexamid 50% WG standalone and Sulphur 80% WG standalone, used as standards for comparison, along with one untreated control.

Tabular presentation of various combinations of Sulphur and Fenhexamid with varying concentration of active ingredients are as follows:

TABLE 1

| Treatment | Compositions | Active ingredient (grams/hectare) | Formulation dosage in gm/ha | Percentage (%) of *Botrytis cyneria* observed DAS. | yield (MT/Ha) |
|---|---|---|---|---|---|
| 1 | Sulphur 20% + Fenhexamid 65% WDG | 400 + 1300 | 2000 | 5 | 21.4 |
| 2 | Sulphur 45% + Fenhexamid 40% WDG | 900 + 800 | 2000 | 6 | 20.8 |
| 3 | Sulphur 55% + Fenhexamid 35% WDG | 1100 + 700 | 2000 | 3 | 23.3 |
| 4 | Sulphur 60% + Fenhexamid 25% WDG | 1200 + 500 | 2000 | 8 | 19.8 |
| 5 | Sulphur 30% + Fenhexamid 25% SC | 600 + 500 | 2000 | 5 | 21.2 |
| 6 | Sulphur 17.5% + Fenhexamid 12.5% SC | 350 + 250 | 2000 | 10 | 19.4 |
| 7 | Sulphur 80% WG | 1250 | 1500 | 12 | 20.7 |
| 8 | Fenhexamid 50% WDG | 750 | 1500 | 7 | 21.5 |
| 9 | Untreated control | — | — | 38 | 18.5 |

From the above table, it can be seen that a significant reduction in disease (*Botrytis cyneria*) severity was noticed with the application of Sulphur 55%+Fenhexamid 35% WDG at 1100+700 g.a.i. per ha (Treatment 3). A reduction in disease severity was also observed on applications of Sulphur 20%+Fenhexamid 65% WDG at 400+1300 g.a.i. per ha (Treatment 1) and Sulphur 45%+Fenhexamid 40% WDG at 900+800 g.a.i. per ha (Treatment 2). The disease severity observed is considerably reduced with Treatments 2 and 3 at low rates of application as compared to the standalone applications of Sulphur 80% WG (Treatment 7) and Fenhexamid 50% WDG (Treatment 8).

A highly effective control over the disease was also observed with Sulphur 30%+Fenhexamid 25% SC at 600+500 gm a.i. per ha (Treatment 5). The composition also demonstrated enhanced protection for a longer duration with a reduced dosage of the active ingredients as compared to the individual use of the actives as seen in Treatments 7 and 8.

The presence of Sulphur in the composition also resulted in high quality berries. The data also shows that the control efficacy was greatly increased by the mixture of the two chemicals, despite being used at very low dosages of the individual active ingredients.

Example 2

Bioefficacy of Sulphur Plus Fenamidone

The field experiment was laid out in Randomized Complete Block Design (RCBD) with 12 treatments and 3 replications in the Nasik district of Maharashtra state on tomato. Tomato seedlings were raised in nursery beds and 21 day old seedlings were transplanted into the field with 60 cms inter and 40 cms intra row spacing in the plots measuring 2 m×2 m. All other cultural and pest control practices were followed as per the recommended practice.

Various combinations of Fenamidone were worked out along with Sulphur for evaluating the strength of the composition in preventing and curating the disease effectively within a certain period of time. The treatments conducted included combinations of Fenamidone with Sulphur in varying concentrations and also included Fenamidone 50% SC standalone and Sulphur 80% WG standalone, used as standards for comparison, along with one untreated control.

The treatments are indicated in the table below:

From the above table, it can be seen that a highly reduced disease (*Alternaria solani*) severity was noticed in treatments with Sulphur 80%+Fenamidone 4% WDG at 1200+60 g.a.i per ha (Treatment 3). A reduction in disease severity was also observed with applications of Sulphur 50%+Fenamidone 20% WDG at 750+300 g.a.i. per ha (Treatment 1) and Sulphur 60%+Fenamidone 8% WDG at 900+120 g.a.i. per ha (Treatment 2) in the form of Water dispersible granules.

It was also observed that the SC formulation of Sulphur 35%+Fenamidone 5% at 525+75 gm a.i. per ha (Treatment 4) provided a highly effective control over the fungus and gave protection for longer duration at a reduced dosage of both Sulphur and Fenamidone in comparison to the individual application of actives at a higher concentrations. (Treatment 6 and 7 respectively)

The disease severity is significantly lowered with the treatments 1 to 5 as compared to Sulphur and Fenamidone used individually (Treatment 6 and 7) thereby indicating a synergistic effect of Sulphur & Fenamidone.

The presence of Sulphur in the composition resulted in high quality produce with an enhanced shine. The treated plots (Treatments 1-5) also showed reduced lodging as compared to the untreated plots.

The data also shows that the control efficacy was greatly increased by the mixture of Sulphur and Fenamidone as compared to the individual use of the two actives. It was also observed that the damage caused by the pathogen was significantly reduced with the compositions containing Sulphur and Fenamidone as against the solo application of both the actives.

Example 3

Bioefficacy of Sulphur Plus Cyazofamid

The treatments conducted included combinations of Cyazofamid with Sulphur in varying concentrations and also included Fenamidone 50% WP standalone and Sulphur 80% WG standalone, used as standards for comparison, along with an untreated control. The treatments as indicated in the Table below were carried out in tomato crop in the Nasik district of Maharashtra state in India:

TABLE 2

| Treatment | Compositions | Active ingredient (grams/hectare) | Formulation dosage in gm/ha | Percentage % of *Alternaria solani* | yield (MT/Ha) |
|---|---|---|---|---|---|
| 1 | Sulphur 50% + Fenamidone 20% WDG | 750 + 300 | 1500 | 5.5 | 21.4 |
| 2 | Sulphur 60% + Fenamidone 8% WDG | 900 + 120 | 1500 | 4 | 20.8 |
| 3 | Sulphur 80% + Fenamidone 4% WDG | 1200 + 60 | 1500 | 3.2 | 23.3 |
| 4 | Sulphur 35% + Fenamidone 5% SC | 525 + 75 | 1500 | 4.6 | 20.8 |
| 5 | Sulphur 25% + Fenamidone 3% SC | 375 + 45 | 1500 | 5.6 | 18.2 |
| 6 | Sulphur 80% WG | 1250 | 1500 | 12.8 | 19.7 |
| 7 | Fenamidone 50% SC | 112.5 | 225 | 7.4 | 20.2 |
| 8 | Untreated control | — | — | 38.3 | 16.3 |

TABLE 3

| Treatments | Compositions | Active ingredient (grams/hectare) | Formulation dosage in gm/ha | Mean % incidence of late blight (7th DAS) | Yield (T/Ha) |
|---|---|---|---|---|---|
| 1 | Sulphur 40% + Cyazofamid 40% WDG | 600 + 600 | 1500 | 8.4 | 20.3 |
| 2 | Sulphur 55% + Cyazofamid 30% WDG | 825 + 450 | 1500 | 0 | 23.7 |
| 3 | Sulphur 50% + Cyazofamid 20% WDG | 750 + 300 | 1500 | 4.7 | 21.3 |
| 4 | Sulphur 75% + Cyazofamid 10% WDG | 1125 + 150 | 1500 | 8.8 | 20.5 |
| 5 | Sulphur 37.5% + Cyazofamid 20% SC | 562.5 + 300 | 1500 | 3.3 | 18.5 |
| 6 | Sulphur 25% + Cyazofamid 2.25% SC | 375 + 112.5 | 1500 | 14.6 | 17.6 |
| 7 | Sulphur 80% WG | 1250 | 1500 | 20.4 | 17.3 |
| 8 | Cyazofamid 50% WP | 300 | 600 | 16.8 | 18.5 |
| 9 | Untreated control | — | — | 32.5 | 13.6 |

Before the treatments, 20-25% of leaves were found affected by the late blight incidence. It was observed after the 5th day of spraying, that application of Sulphur 55%+Cyazofamid 30% WDG at 825+450 a.i gm/ha (Treatment 2) proved to be highly effective as the spores started drying and a reduction in the number of spores was observed since the 5th day after spraying which further diminished on the 7th day after spraying and no new sporulation was observed with the treatment.

It was also observed that the treatment with Sulphur 37.5%+Cyazofamid 20% SC at 562.5+300 g.a.i.per ha (Treatment 5) and Sulphur 50%+Cyazofamid 20% WDG at 750+300 g.a.i.per ha (Treatment 3) showed an effective control despite being used at very low concentrations of the individual active ingredients, particularly sulphur.

In case of application of Sulphur 55%+Cyazofamid 30% WDG at 825+450 a.i gm/ha (Treatment 2), a highly effective control was observed up to 25th DAS, whereas the other applications (Treatments 1, 3 and 4) were found effective up to the 18th DAS and the application of Sulphur 37.5%+Cyazofamid 20% SC at 562.5+300 g.a.i.per ha (Treatment 5) was found to be effective up to 15th to 20th days after spraying with much better control over the late blight incidence in comparison with Treatments 7 and 8. The untreated control was found to be badly damaged by the severity of late blight incidence resulting in a reduced yield.

Example 4

Bioefficacy of Sulphur Plus Chlorothalonil

The trial was conducted in the Junagadh district of Saurashtra area in Gujarat state on Peanut for leaf spot control. Two rows were selected for one treatment and there were total eight treatments including untreated control, which were replicated thrice. Field experiments were conducted to compare the efficacy of mixtures of sulphur and reduced rates of chlorothalonil with that of full rates of chlorothalonil alone and sulphur alone for comparison, along with an untreated control.

The trials were replicated thrice as indicated in the table below with varying concentration of active ingredients:

TABLE 4

| Treatment | Compositions | Active ingredient (grams/hectare) | Formulation dosage in gm/ha | % Disease index (Mean value) |
|---|---|---|---|---|
| 1 | Sulphur 35% + Chlorothalonil 50% WDG | 700 + 1000 | 2000 | 16.5 |
| 2 | Sulphur 60% + chlorothalonil 25% WDG | 1200 + 500 | 2000 | 8.3 |
| 3 | Sulphur 65% + chlorothalonil 20% WDG | 1300 + 400 | 2000 | 12.8 |
| 4 | Sulphur 70% + chlorothalonil 15% WDG | 1400 + 300 | 2000 | 18.6 |
| 5 | Sulphur 35% + chlorothalonil 15% SC | 700 + 300 | 2000 | 11.4 |
| 6 | Sulphur 25% + chlorothalonil 7.5% SC | 500 + 150 | 2000 | 21.7 |
| 7 | Sulphur 80% WG | 1250 | 1500 | 30.6 |
| 8 | Chlorothalonil 75% WP | 761.5 | 1015 | 28.2 |
| 9 | Untreated control | — | — | 60.5 |

From the above table, an excellent disease control was noticed with Sulphur 60%+Chlorothalonil 25% WDG at 1200+500 g.a.i. per ha (Treatment 2) with reduced amounts of active ingredients, which is significantly better when compared with the stand alone applications of either Sulphur (Treatment 7) or Chlorothalonil (Treatment 8) at higher dosages of the active ingredients.

The synergistic role of Sulphur and Chlorothalonil in the composition was clearly observed with the application of Sulphur 60%+chlorothalonil 25% WDG at 1200+500 g.a.i. per ha (Treatment 2)

The application of Sulphur 60%+Chlorothalonil 25% WDG at 1200+500 g.a.i. per ha (Treatment 2) proved better as compared to the individual application of Sulphur at a higher concentration (Treatment 7) not only in managing the lower disease index but also adding to the increased pod yield and the oil content.

It was also observed that application of Sulphur 35%+Chlorothalonil 15% SC at 700+300 g.a.i. per ha (Treatment 5) reduced the disease index considerably and was found to be effective till the 15th day after spraying even in the congineal and favourable environmental condition as compared to the stand alone applications of either Sulphur (Treatment 7) or Chlorothalonil (Treatment 8) at higher dosages.

First spraying was carried out for the control of early and late leaf spot. A highly effective control was observed in the treatments of combinations of Sulphur 60%+Chlorothalonil 25% WDG at 1200+500 gm a.i per ha (Treatment 2), which was followed by the other three treatments (Treatments 5, 3, 1 and 4) which were found at par with each other after the 12th DAS.

A highly effective leaf spot control for 20 to 25 days was observed in the case of Treatment 2. Moreover it was observed that the composition enhanced the foliage (darker greenish leaves) and induced chlorophyll formation in the plants.

Example 5

Bioefficacy of Sulphur Plus Kresoxim Methyl

The experiment was conducted in the Nasik district of Maharashtra state in India with seven treatments and four replications. Each treatment was applied to two vine/grape plant with 35% to 40% downy mildew infestation, prior to conducting the trial.

The treatments applied were as follows:
1. Sulphur 40%+Kresoxim methyl 40% WDG at 600+600 gm a.i per ha
2. Sulphur 60%+Kresoxim methyl 24% WDG at 900+360 gm a.i per ha
3. Sulphur 70%+Kresoxim methyl 10% WDG at 1050+150 gm a.i per ha
4. Sulphur 35%+Kresoxim methyl 20% SC at 540+300 gm a.i per ha
5. Sulphur 25%+Kresoxim methyl 11% SC at 375+165 gm a.i per ha
6. Sulphur 80% WG at 1250 gm a.i per ha
7. Kresoxim methyl 44.3% SC at 300 gm a.i per hecatre
8. Untreated control For the treatments 1 to 6, the dosage per hectare was kept 1500 gm per hectare with varying concentration of active ingredients applied in each treatment. These treatments were compared with Sulphur 80% WG stand alone and Kresoxim methyl 44.3% SC standalone and an untreated control.

It was observed that Sulphur 40%+Kresoxim methyl 40% WDG at 600+600 (Treatment 1) and Sulphur 60%+Kresoxim methyl 24% WDG at 900+360 g a.i per ha (Treatment 2), were highly effective in controlling the downy mildew fungus effectively up to the 20th DAS as compared to the individual applications of Sulphur 80% WG at 1250 gm a.i per ha (Treatment 6) and Kresoxim methyl 44.3% SC at 300 gm a.i per hectare (Treatment 7).

The treatment with Sulphur 70%+Kresoxim methyl 10% WDG at 1050+150 g a.i. per hectare (Treatment 3) was effective than Kresoxim methyl 44.3SC used alone (Treatment 7) and gave the control up to 15th DAS effectively. The combination with reduced amounts of active ingredients was found effective than the Kresoxim methyl used alone in inhibiting the growth of downy mildew fungus.

Further Sulphur 35%+Kresoxim methyl 20% SC at 540+300 gm a.i per ha (Treatment 4), proved significantly effective in suppressing the downy mildew spores effectively up to 12th day after spraying as compared to the standalone applications of both Sulphur and Kresoxim methyl at higher concentrations.

The foliar applications of Sulphur+Kresoxim methyl, 2 weeks apart, to field-grown grapevines inhibited downy mildew development to a considerable extent.

The combination showed strong prophylactic and local activity in intact plants and detached leaf disks. The suppression of *Plasmopara viticola* was also demonstrated by the reduction of the number of existing colonies when the compositions were applied to the infested leaves. The inhibitory effectiveness of Sulphur+Kresoxim methyl makes it well suited for integration into control programs against powdery and downy mildew diseases in vineyards, and as a component of resistance avoidance strategies in both powdery and downy mildew management.

Example 6

Bioefficacy of Sulphur Plus Azoxystrobin

The treatments included compositions of Sulphur plus Azoxystrobin at varying concentration of the active ingredients; Sulphur 80% WG standalone and Azoxystrobin 23% SC standalone as standards for comparison along with an untreated control. Eight treatments were experimented with four replications by keeping three vines for each treatment. The treatments were carried out in grapes in the Sangli district of Maharashtra state and are as indicated in the table below:

Before the spray, around 35% to 40% of leaves were found affected by the Powdery mildew incidence.

TABLE 5

| Treatment | Compositions | Active ingredient (grams/hectare) | Formulation dosage in gm/ha | Mean % incidence of powdery mildew | Yield (T/Ha) |
|---|---|---|---|---|---|
| 1 | Sulphur 50% + Azoxystrobin 20% WDG | 750 + 300 | 1500 | 12 | 20.6 |
| 2 | Sulphur 65% + Azoxystrobin 9% WDG | 975 + 135 | 1500 | 7 | 21.0 |
| 3 | Sulphur 80% + Azoxystrobin 5% WDG | 1200 + 75 | 1500 | 0 | 23.7 |
| 4 | Sulphur 35% + Azoxystrobin 10% SC | 525 + 150 | 1500 | 4 | 22.3 |
| 5 | Sulphur 25% + Azoxystrobin 3% SC | 375 + 45 | 1500 | 17 | 17.3 |
| 6 | Sulphur 80% WG | 1250 | 1500 | 20 | 17.0 |
| 7 | Azoxystrobin 23% SC | 125 | 1500 | 16 | 17.5 |
| 8 | Untreated control | — | — | 32 | 14.3 |

It was observed that after the 5th day of spraying, the application of Sulphur 80%+Azoxystrobin 5% WDG at 1200+75 a.i gm per ha (Treatment 3) and Sulphur 35%+Azoxystrobin 10% SC at 525+150 g a.i per hectare (Treatment 4), showed a highly effective disease control as the spores started drying and no further spore development was observed.

Further the treatments with Sulphur 50%+Azoxystrobin 20% WDG at 750+300 g a.i per hectare (Treatment 1) and Sulphur 65%+Azoxystrobin 9% WDG at 975+135 g a.i per hectare (Treatment 2) also provided good control of the disease infestation as compared to the individual application of Sulphur (Treatment 6) and Azoxystrobin 23% SC (Treatment 7).

It was noted that the application of Sulphur 80%+Azoxystrobin 5% WDG at 1200+75 a.i gm per ha (Treatment 3), effectively controlled the infestation up to the 25th DAS, whereas the other treatments were found effective up to 18th DAS. The treatment with azoxystrobin 23% SC (Treatment 7), was found effective only up to the 12th DAS.

The untreated control was badly damaged by the severity of Powdery mildew incidence. Besides the untreated control exhibited a carry forward of the downy mildew infection.

Example 7

Bioefficacy of Sulphur Plus Pyraclostrobin

The trial were conducted on grapes in the state of Karnataka in India with the treatments as indicated in the table below including compositions of Sulphur plus Praclostrobin at varying concentrations, Sulphur 80% WG stand alone treatment and Pyraclostrobin 20% WG stand alone as standards for comparison, along with an untreated control. The treatments were laid out on a randomized block design with first seven treatments replicated thrice in the test variety Bangalore blue.

Three sprays of the treatments were applied at an interval of 15 days starting with the initiation of reproductive inflorescence. The observations on Powdery mildew were recorded, 10 days after the 3rd spray using 0-5 scale. The percentage disease incidence was calculated using the formula given by Mac Kinny. The disease severity and the yield data were statistically analyzed.

TABLE 6

| Treatment | Compositions | Active ingredient (grams/hectare) | Formulation dosage in gm/ha | Mean % incidence of powdery mildew(7th DAS) | Yield (T/Ha) |
|---|---|---|---|---|---|
| 1 | Sulphur 60% + Pyraclostrobin 15% WDG | 600 + 150 | 1000 | 12 | 20.2 |
| 2 | Sulphur 70% + Pyraclostrobin 10% WDG | 700 + 100 | 1000 | 8 | 24.8 |
| 3 | Sulphur 75% + Pyraclostrobin 7% WDG | 750 + 70 | 1000 | 15 | 18.4 |
| 4 | Sulphur 37.5% + Pyraclostrobin 7.5% SC | 375 + 75 | 1000 | 12 | 22.7 |
| 5 | Sulphur 30% + Pyraclostrobin 3.5% SC | 300 + 35 | 1000 | 22 | 18.4 |
| 6 | Sulphur 80% WG | 1250 | 1500 | 30 | 17.4 |
| 7 | Pyraclostrobin 20% WG | 100 | 250 | 21 | 18.8 |
| 8 | Untreated control | — | — | 42 | 10.2 |

From the above table, a very high control of the disease severity was observed with the application of Sulphur 70%+ Pyraclostrobin 10% WDG at 700+100 g.a.i. per ha (Treatment 2) which is significant reduction in disease severity as compared to the individual application of Sulphur and Pyraclostrobin (Treatment 6 and 7), showing the synergistic effect between Sulphur and Pyraclostrobin.

It was also observed that the Sulphur 37.5%+Pyraclostrobin 7.5% SC at 375+75 g.a.i per ha (Treatment 4) at reduced concentrations of actives showed a significant reduction in disease severity as compared to the individual application of actives at higher concentrations (Treatments 6 and 7 respectively).

It was also noticed that the compositions of Sulphur and Pyraclostrobin exhibited a positive effect on the sulphur nutritional requirements as compared to the individual application of the actives.

The data also shows management of bunch rot, disease which persists all through the crop season in treatments with SC and WG compositions of Sulphur and Pyraclostrobin.

Example 9

Bioefficacy of Sulphur Plus Iprodione

The trials were conducted on grapes in the Sangli district of Maharashtra state in India with compositions of Sulphur and Iprodione in varying concentrations of the active ingredients, along with Sulphur 80% WG standalone and Iprodione 50% WP standalone used alone as a standard for comparison along with an untreated control. The treatments were as indicated in the table below:

The treatments were laid out on a randomized block design with each nine treatment replicated thrice in the test variety Tas ganesh. Three treatments of the fungicides were given at an interval of 15 days starting with the initiation of reproductive inflorescence.

The disease severity and the yield data were statistically analyzed.

From the above table, a reduction in disease severity was observed with the application of Sulphur 40%+Iprodione 45% WDG at 800+900 g.a.i per ha (Treatment 3) followed by treatment with Sulphur 55%+Iprodione 30% WDG at 1100+600 g.a.i per ha (Treatment 4) which was significant reduction in disease severity as compared to the two actives used individually at higher concentrations.

It was also observed that application of Sulphur 27.5%+ Iprodione 25% SC at 550+500 g a.i per ha (Treatment 5) proved to be highly effective with reduced dosage of the active ingredients over an extended period of time as compared to the individual application of the actives at a higher concentration.

It was also noticed that the compositions of Sulphur and Iprodione had a positive influence on reducing the damage caused by the disease infestation and also exhibited a positive effect of nutritional quality of the produce.

The data also shows that the composition shows enhanced efficacy of managing not only the bunch rot but also powdery mildew as compared to the individual actives at higher concentrations.

Example 10

Bioefficacy of Sulphur Plus Validamycin

The trials were conducted on paddy in the State of Andhra Pradesh in India with Sulphur and Validamycin in varying concentration of active ingredients with Sulphur 80 WG used alone and Validamycin 3% L used alone as standard, along with an untreated control. The treatments were as in the table below.

The eight treatments were laid out on a randomized block design with the treatments replicated thrice in the test variety Masuri. Two sprays of the treatment were given on the 40th and the 60th days after transplanting. The assessment of sheath blight disease severity was made by following standard evaluation system scale (IRRI, 1996) on the 55th and the 75th days after transplanting.

TABLE 7

| Treatment | Compositions | Active ingredient (grams/Hectare) | Formulation dosage in gm/ha | Mean % incidence of powdery mildew | Mean % incidence of Bunch rot | Yield (T/Ha) |
| --- | --- | --- | --- | --- | --- | --- |
| 1 | Sulphur 25% + Iprodione 60% WDG | 500 + 1200 | 2000 | 36 | 28 | 18.2 |
| 2 | Sulphur 45% + Iprodione 40% WDG | 900 + 800 | 2000 | 35 | 25 | 16.3 |
| 3 | Sulphur 40% + Iprodione 45% WDG | 800 + 900 | 2000 | 18 | 13 | 25.8 |
| 4 | Sulphur 55% + Iprodione 30% WDG | 1100 + 600 | 2000 | 20 | 18 | 23.6 |
| 5 | Sulphur 27.5% + Iprodione 25% SC | 550 + 500 | 2000 | 21 | 20 | 21.3 |
| 6 | Sulphur 17.5% + Iprodione 15% SC | 350 + 300 | 2000 | 38 | 37 | 16.7 |
| 7 | Control - Sulphur 80% WG | 1250 | 1500 | 35 | 15 | 15.6 |
| 8 | Control - iprodione 50% WP | 400 | 800 | 36 | 18 | 15.2 |
| 9 | Untreated control | — | — | 58 | 46 | 7.9 |

TABLE 8

| Treatments | Compositions | Active ingredient (grams/ hectare) | Formulation dosage in gm/ha | % disease severity on leaf | Grain yield (kg/Ha) |
|---|---|---|---|---|---|
| 1 | Sulphur 50% + Validamycin 10% WDG | 750 + 150 | 1500 | 12 | 3865 |
| 2 | Sulphur 60% + Validamycin 5% WDG | 900 + 75 | 1500 | 8 | 4000 |
| 3 | Sulphur 70% + Validamycin 4% WDG | 1050 + 60 | 1500 | 15 | 3770 |
| 4 | Sulphur 80% + Validamycin 3% WDG | 1200 + 45 | 1500 | 16 | 3685 |
| 5 | Sulphur 36% + Validamycin 2.5% SC | 600 + 37.5 | 1500 | 10 | 3905 |
| 6 | Sulphur 25% + Validamycin 1.5% SC | 375 + 22.5 | 1500 | 20 | 3600 |
| 7 | Sulphur 80% WG | 1250 | 1500 | 30 | 3580 |
| 8 | Validamycin 3% Liquid | 60 | 2000 | 19 | 3606 |
| 9 | Untreated control | — | — | 38 | 2150 |

From the above table, a highly reduced disease severity was observed with the application of Sulphur 60%+Validamycin 5% WDG at 900+75 g.a.i. per ha (Treatment 2).

A very effective disease control and a higher yield was noticed with the application of Sulphur 36%+Validamycin 2.5% SC at 600+37.5 g.a.i. per ha (Treatment 5) as compared to the individual applications of Sulphur and Validamycin at higher concentrations (Treatment 7 and Treatment 8 respectively).

It was also noticed that the Treatments 1 to 6 had a positive influence on the nutritional value of the produce resulting in high quality, shining grains.

It was noted that the presence of Sulphur in the composition also enhanced the grain quality. Since the trial was conducted on high value aromatic cultivar of rice generally prone to lodging, it was noted that the plots treated with Sulphur and Validamycin compositions exhibited no lodging at all.

The data also showed that the control efficacy was greatly increased by the sulphur and validamycin compositions as against their individual applications at higher dosages. Apart from this, the presence of sulphur in the composition provided an improved foliage, the green colour of the leaves was enhanced and the leaves had a completely open lamina.

Example 11

Bioefficacy of Sulphur Plus Kasugamycin

The trials were conducted on paddy in the State of Andhra Pradesh with the treatments as indicated in the table below. The eight treatments were laid out on a randomized block design with each treatment replicated thrice in the test variety Masuri. Two sprays of the treatments were applied on the 40th and the 60th days after transplanting. The assessment of Neck blast disease severity was made by following standard evaluation system scale (IRRI, 1996) on the 55th and 75th days after transplanting.

TABLE 9

| Treatment | Compositions | Active ingredient (grams/ hectare) | Formulation dosage in gm/ha | % disease severity of neck blast | Grain yield (kg/Ha) |
|---|---|---|---|---|---|
| 1 | Sulphur 50% + Kasugamycin 10% WDG | 750 + 150 | 1500 | 10.2 | 3900 |
| 2 | Sulphur 60% + Kasugamycin 5% WDG | 900 + 75 | 1500 | 8.3 | 4000 |
| 3 | Sulphur 70% + Kasugamycin 4% WDG | 1050 + 60 | 1500 | 13.8 | 3770 |
| 4 | Sulphur 80% + Kasugamycin 1.5% WDG | 1200 + 22.5 | 1500 | 17.3 | 3685 |
| 5 | Sulphur 40% + Kasugamycin 2.5% SC | 540 + 37.5 | 1500 | 13.5 | 3705 |
| 6 | Sulphur 25% + Kasugamycin 1.5% SC | 375 + 22.5 | 1500 | 22.5 | 3476 |
| 7 | Sulphur 80% WG | 1250 | 1500 | 30 | 3480 |
| 8 | Kasugamycin 3% L | 40 | 1333 | 20 | 3501 |
| 9 | Untreated control | — | — | 38 | 2150 |

From the above table, a significantly reduced disease severity was noticed with the application of Sulphur 60%+Kasugamycin 5% WDG at 900+75 g.a.i per ha (Treatment 2) as against the application of two actives used singly (Treatment 7 and Treatment 8 respectively). The application of Sulphur 50%+Kasugamycin 10% WDG at 750+150 g.a.i per ha (Treatment 1) also provided an effective control over the neck blast disease.

It was also noticed that the compositions of Sulphur and Kasugamycin had a positive influence on reducing the damage caused by severe mite infestation and leaf blight and a positive effect on the nutritional value resulting in high quality, shining grains. Since the trial was conducted on high value aromatic cultivar of rice generally prone to lodging, no lodging was observed on the plots treated with the compositions of Sulphur and Kasugamycin.

It was also observed that Sulphur 40%+Kasugamycin 2.5% SC 540+37.5 g.a.i per ha (Treatment 5) was very effective in controlling the blast as compared to the individual application of the actives at higher concentrations Example 12

Bioefficacy of Sulphur Plus Cyprodinil

The field trials were carried out in a commercial vineyard in Nasik district of Maharashtra state in India. The vines were moderately vigorous, cordon-trained, spur-pruned, and planted on a spacing of 8×12 feet (vine×row). A 2×5 split-plot design with four replicates was used to carry out the trial.

The treatments applied were as follows:
1. Sulphur 50%+Cyprodinil 30% WDG at 750+450 a.i gm per ha
2. Sulphur 65%+Cyprodinil 20% WDG at 975+300 a.i gm per ha
3. Sulphur70%+Cyprodinil 15% WDG at 1050+225 a.i gm per ha
4. Sulphur 70%+Cyprodinil 10% WDG at 1050+150 a.i gm per ha
5. Sulphur 35%+Cyprodinil 10% SC at 525+150 a.i gm per ha
6. Sulphur 25%+Cyprodinil 5% SC at 375+75 a.i gm per ha
7. Cyprodinil 75% WG at 245 gm a.i per ha
8. Sulphur 80% WG at 1250 gm a.i per ha
9. Untreated control For the treatments 1 to 6, the dosage per hectare was kept at 1500 gm per hectare with respect to the varying of Sulphur and Cyprodinil in each treatment. All the treatments were compared with the individual actives used alone and the untreated control.

As per the spray schedule the precautionary measures were taken in grapes and by considering the favourable weather conditions, the above mentioned treatments were sprayed accordingly.

It was observed that the treatment with Sulphur 65%+Cyprodinil 20% WDG at 975+300 g.a.i per ha (Treatment 2) proved highly effective in controlling the bunchy rot in comparison with the individual actives sulphur and cyprodinil applied alone (Treatment 7 and Treatment 8 respectively). The application of Sulphur 70%+Cyprodinil 15% WDG at 1050+225 g.a.i per ha (Treatment 4) also showed an enhanced control of the disease infestation till the time of harvest.

It was also observed that Sulphur 35%+Cyprodinil 10% SC at 525+150 gm a.i per ha (Treatment 5) provided a good control of the bunchy top disease in comparison with the individual application of the actives at higher doses.

Post harvest the berries were kept under storage at 5° C. for 28 to 30 days and it was observed that the symptoms were not noticed in the berries subjected to Treatments 1-3. However, 8 to 10% bunchy rot was noticed in the berries subjected to Treatment 4. The untreated control was highly infested before the berries were harvested and bunchy rot covered almost more than 80% of the untreated berries.

Example 13

Bioefficacy of Sulphur Plus Pencycuron

The field studies were conducted to test the bio-efficacy of Sulphur+Pencycuron with varying concentrations and Pencycuron 75% WP alone and Sulphur 80% WG alone as standard along with an untreated control against the sheath blight of paddy at the Agricultural Research Station, at Raipur in Chattisgarh (India).

The treatments were carried out in a randomized block design with six treatments replicated thrice in the test variety Jyothi. Two sprays of the treatments were given on the 50th and the 70th days after transplanting.

The treatments applied were as indicated in the table below:

TABLE 10

| Treatment | Compositions | Active ingredient (grams/hectare) | Formulation Dosage in grams/hectare | % Disease severity of sheath blight | Grain yield per hectare |
|---|---|---|---|---|---|
| 1 | Sulphur 50% + Pencycuron 30% WDG | 750 + 450 | 1500 | 3.25 | 5737 |
| 2 | Sulphur 70% + Pencycuron 12.5% WDG | 1050 + 187.5 | 1500 | 4.76 | 5712 |
| 3 | Sulphur 70% + Pencycuron 6% WDG | 1050 + 90 | 1500 | 10.28 | 5263 |
| 4 | Sulphur 35% + Pencycuron 15% SC | 525 + 225 | 1500 | 5.37 | 5218 |
| 5 | Sulphur 25% + Pencycuron 5% SC | 375 + 75 | 1500 | 13.67 | 4936 |
| 6 | Sulphur 80% WG | 1250 | 1500 | 25.52 | 4893 |
| 7 | Pencycuron 75% WP | 168.75 | 735 | 22.48 | 5017 |
| 8 | Untreated control | — | — | 32.79 | 4004 |

The table indicates that application of Sulphur 70%+Pencycuron 12.5% WDG at 1050+187.5 g a.i per ha (Treatment 2) was found to be highly effective in controlling sheath blight with only 4% disease incidence after the 12th day of application. An increased grain yield (5712 kg/ha) was also observed when compared to the untreated check (4004 kg/ha).

It can be concluded that a significantly reduced disease severity was noticed with applications of Sulphur 50%+Pencycuron 30% WDG at 750+450 g.a.i per ha (Treatment 1); Sulphur 70%+Pencycuron 12.5% WDG at 1050+187.5 g.a.i per ha (Treatment 2) and Sulphur 70%+Pencycuron 6% WDG at 1050+90 g.a.i per ha (Treatment 3) respectively.

This disease severity observed was significantly lower than the two actives Sulphur and Pencycuron used alone at higher concentrations (Treatments 6 and Treatment 7 respectively). It was also noticed that the compositions of Sulphur and Pencycuron had a positive influence on reducing the damage caused by the disease infestation.

It was further observed that the application of Sulphur 35%+Pencycuron 15% SC at 525+225 g a.i per ha (Treatment 4) was very effective in curing sheath blight up to a satisfactory level for a comparative longer period of time, in comparison to the individual application of actives at higher concentrations.

In addition to enhanced efficacy and increased yield, all the combination treatments including Sulphur exhibited enhanced phytotonic effect with improved foliage (green and luxuriant growth.)

Example 14

Bioefficacy of Sulphur Plus Hexaconazole

The trials were carried in the State of Uttar Pradesh with Sulphur and Hexaconazole in combination with varying concentration of the active ingredients along with treatments with Sulphur 80% WG and Hexaconazole 5% SC for comparison along with an untreated control.

The eight treatments were laid out on a randomized block design with each treatment replicated thrice in the test variety (Amrapali) of Mango. The treatments were as illustrated in the table below:

Three sprays of the treatments were given at an interval of 15 days starting with the initiation of reproductive inflorescence. The observations on Powdery mildew were recorded 10 days after the 3rd spray using 0-5 scale. The percentage of disease incidence was calculated using the formula given by Mac Kinny. The disease severity and the yield data were statistically analyzed.

A highly effective control of the disease infestation was also noted with Sulphur 40%+Hexaconazole 4% SC at 600+60 g.a.i per ha (Treatment 5) with least disease percentage observed after the 12th day of spraying as compared to the use of the two actives individually at a higher concentration.

It was also observed that the presence of Sulphur in the composition enhanced the yield resulting in high quality fruits. The data shows that the control efficacy was enhanced by the mixture of the two chemicals as compared to their single use.

Example 15

Bioefficacy of Sulphur Plus Prochloraz

The trial was evaluated in Saharanpur district of Uttar Pradesh in India on mango (*Mangifera indica*) with eight treatments and four replications to control powdery mildew and by the pre harvest spray of the same combination again, to get its impact on post harvest disease also. The treatments included applications of combinations of Sulphur and Prochloraz in varying percentages of the active ingredients, with Sulphur 80% WG standalone and Prochloraz 45% EC

TABLE 11

| Treatments | Compositions | Active ingredient (grams/hectare) | Formulation Dosage in grams/hectare | Mean % incidence of powdery mildew(7th DAS) | Yield (T/Ha) |
|---|---|---|---|---|---|
| 1 | Sulphur 60% + hexaconazole 8% WDG | 900 + 120 | 1500 | 8.3 | 3.00 |
| 2 | Sulphur 70% + hexaconazole 5% WDG | 1050 + 75 | 1500 | 10.4 | 2.77 |
| 3 | Sulphur 75% + hexaconazole 4% WDG | 1125 + 60 | 1500 | 12.7 | 2.72 |
| 4 | Sulphur 80% + hexaconazole 2% WDG | 1200 + 30 | 1500 | 15.8 | 2.56 |
| 5 | Sulphur 40% + hexaconazole 4% SC | 600 + 60 | 1500 | 11.2 | 2.82 |
| 6 | Sulphur 30% + hexaconazole 1.5% SC | 450 + 22.5 | 1500 | 14.2 | 2.45 |
| 7 | Sulphur 80% WG | 1250 | 1500 | 18.2 | 2.55 |
| 8 | Hexaconazole 5% SC | 50 | 500 | 13.6 | 2.5 |
| 9 | Untreated control | — | — | 38.4 | 0.93 |

From the above table a significantly reduced disease severity was noticed with Sulphur 60%+Hexaconazole 8% WDG at 900+120 g.a.i per ha (Treatment 1).

standalone as standards for comparison, along with an untreated control. The treatments were as indicated in the table below:

TABLE 12

| Treatment | Composition | Active ingredient (grams/hectare) | Formulation Dosage in grams/hectare | Mean % incidence of Powdery mildew |
|---|---|---|---|---|
| 1 | Sulphur 25% + Prochloraz 60% WDG | 500 + 1200 | 2000 | 21.53 |
| 2 | Sulphur 50% + Prochloraz 30% WDG | 1000 + 600 | 2000 | 18.62 |

TABLE 12-continued

| Treatment | Composition | Active ingredient (grams/hectare) | Formulation Dosage in grams/hectare | Mean % incidence of Powdery mildew |
|---|---|---|---|---|
| 3 | Sulphur 55% + Prochloraz 25% WDG | 1100 + 500 | 2000 | 8.76 |
| 4 | Sulphur 70% + Prochloraz 10% WDG | 1400 + 200 | 2000 | 5.32 |
| 5 | Sulphur 27.5% + Prochloraz 30% SC | 550 + 600 | 2000 | 6.47 |
| 6 | Sulphur 20% + Prochloraz 12.5% SC | 400 + 250 | 2000 | 27.35 |
| 7 | Sulphur 80% WG | 1250 | 1500 | 13.47 |
| 8 | Prochloraz 45% EC | 500 | 1100 | 22.48 |
| 9 | Untreated control | — | — | 44.68 |

All the combinations of Sulphur+Prochloraz were sprayed at different phases of the mango cropping season. Sulphur+Prochloraz at various combinations were evaluated for the disease controlling efficiency on Anthracnose and Powdery mildew. No toxicity was noted on the leaves, flowers or fruit for any of the chemicals tested.

The first spraying was conducted for the control of Powdery mildew at the flowering stage. It was observed that treatment with Sulphur 70%+Prochloraz 10% WDG with 1400+200 g.a.i. per ha (Treatment 4) gave a highly effective control as compared to the individual application of Sulphur 80% WG (Treatment 7) and Prochloraz 45% EC (Treatment 8) at higher concentrations.

The treatment with Sulphur 27.5%+Prochloraz 30% SC at 550+600 g.a.i.per ha (Treatment 5) was also found effective in controlling the powdery mildew infestation despite being used at very low dosages of the individual active ingredients.

The other treatments were found at par with each other after the 12th DAS. Besides the presence of Sulphur in the composition resulted in an improved foliage with leaves which are more greenish in colour with the leaf lamina completely opened as compared to non Sulphur sprayed treatments.

The treatments were also sprayed pre-harvest (before 45 days of harvest) to see its impact on anthracnose and stem rot. The trials were also conducted on post harvested fruits. The post harvest diseases (anthracnose and stem-end rot) were controlled efficiently by the pre harvest spray of Sulpur+Prochloraz at varying concentrations up to 30 to 40 percent over the untreated control.

Example 16

Bioefficacy of Sulphur Plus Epoxiconazole

The trials were carried out in State of Karnal district of Haryana in India with compositions consisting of Sulphur and Epoxiconazole in combinations with varying concentration of active ingredients. The treatments also included applications of Epoxiconazole 25.9% EC and Sulphur 80% WG and an untreated control. The treatments were laid out on a randomized block design with each of the eight treatment replicated in the test variety Sonalika of wheat. Two sprays of the treatments were given on the 50th and the 70th days after sowing to coincide with the early appearance of leaf rust symptoms. The assessment of disease severity was made by following standard evaluation system scale on the 50th and the 70th days after sowing. The treatments applied were as indicated in the table below:

TABLE 13

| Treatment | Compositions | Active ingredient (grams/hectare) | Formulation Dosage in grams/hectare | Mean % Disease severity on leaf rust |
|---|---|---|---|---|
| 1 | Sulphur 60% + Epoxiconazole 20% WDG | 720 + 240 | 1200 | 7.5 |
| 2 | Sulphur 70% + Epoxiconazole 10% WDG | 840 + 120 | 1200 | 5.3 |
| 3 | Sulphur 75% + Epoxiconazole 4% WDG | 900 + 48 | 1200 | 8.6 |
| 4 | Sulphur 80% + Epoxiconazole 3% WDG | 960 + 36 | 1200 | 12.3 |
| 5 | Sulphur 70% + Epoxiconazole 10% SC | 840 + 120 | 1200 | 6.2 |
| 6 | Sulphur 30% + Epoxiconazole 1.5% SC | 360 + 18 | 1200 | 17.4 |
| 7 | Sulphur 80% WG | 1250 | 1500 | 22.7 |
| 8 | Epoxiconazole 25.9% EC | 150 | 500 ml | 18.3 |
| 9 | Untreated control | — | — | 45.4 |

From the above table, a very low disease severity was observed with the application of Sulphur 70%+Epoxiconazole 10% WDG at 840+120 g.a.i. per ha (Treatment 2). This disease severity was significantly lower than the Sulphur and Epoxiconazole standalone applications (Treatments 7 and 8 respectively) It was also noticed that the combination treatments (1-6) had a positive influence on reducing the damage not only of leaf rust but other fungal pathogens that occurs at varying extents and at different vegetative stages of the crop growth.

The data also shows that the control efficacy was greatly increased by the mixture of Sulphur and Epoxiconazole in a composition at a reduced dosage as against their individual use at higher concentrations.

It was also observed that Sulphur 70%+Epoxiconazole 10% WDG at 840+120 g.a.i. per ha (Treatment 2) also resulted in an increased yield suggesting the possibility of advantageous influence on metabolism with higher plants.

In case of SC formulation, it was observed that the application of Sulphur 70%+Epoxiconazole 10% SC at 840+120 g.a.i.per ha (Treatment 5), was extremely effective in reducing the leaf rust disease incidence as compared to the individual application of the actives at higher concentration after the same period of time, after the spray schedule.

Example 17

Bioefficacy of Sulphur Plus Prothioconazole

The trial was conducted on wheat in the Hissar district of Haryana state in India with nine treatments replicated thrice by adopting uniform agronomic practices for all the replications and treatments. The treatments with varying concentration of Sulphur and Prothioconazole in combination as well as individual applications of the active and the untreated control were conducted as indicated in the table below:

The presence of sulphur in the composition also resulted in an enhanced grain quality. Since the trial was conducted on high value Duram cultivar of wheat, it was noted that the plots treated with sulphur and prothioconazole compositions exhibited no lodging at all.

It was also observed that treatment with Sulphur 35%+ Prothioconazole 30% SC at 700+600 g.a.i per ha (Treatment 6) proved highly effective as compared to the individual applications of Sulphur and Prothioconazole (Treatments 8 and 9 respectively) in reducing and controlling the *Fusarium* head blight for longer duration.

The data also shows that the control efficacy was greatly increased by compositions comprising mixtures of Sulphur and Prothioconazole.

Example 18

Bioefficacy of Sulphur Plus Thiophanate Methyl

The trials were conducted in the Saharanpur district of Uttar Pradesh in India. Eight treatments with four replica

TABLE 14

| Treatments | Compositions | Active ingredient Dosage in (grams/ hectare) | Formulation Dosage in grams/ hectare | Percentage (%) of *fusarium* head blight |
| --- | --- | --- | --- | --- |
| 1 | Sulphur 25% + Prothioconazole 60% WDG | 500 + 1200 | 2000 | 5.75 |
| 2 | Sulphur 50% + Prothioconazole 30% WDG | 1000 + 600 | 2000 | 6.37 |
| 3 | Sulphur 55% + Prothioconazole 25% WDG | 1100 + 500 | 2000 | 3.36 |
| 4 | Sulphur 60% + Prothioconazole 20% WDG | 1200 + 400 | 2000 | 8.34 |
| 5 | Sulphur 70% + Prothioconazole 5% WDG | 1400 + 100 | 2000 | 8.92 |
| 6 | Sulphur 35% + Prothioconazole 30% SC | 700 + 600 | 2000 | 6.58 |
| 7 | Sulphur 20% + Prothioconazole 5% SC | 400 + 100 | 2000 | 10.51 |
| 8 | Sulphur 80% WG | 1250 | 1500 | 15.15 |
| 9 | Prothioconazole 25% EC | 400 | 1600 | 8.67 |
| 10 | Untreated control | | | 38.83 |

From the above table, a significant reduction in disease severity was noticed in Sulphur 55%+Prothioconazole 25% WDG at 1100+500 g.a.i. per ha (Treatment 3).

The disease severity was also found to be reduced with the application of Sulphur 25%+Prothioconazole 60% WDG at 500+1200 g.a.i.per ha (Treatment 1).

tions of Thiophanate methyl combinations with Sulphur and Thiophanate methyl 70% WP stand alone, Sulphur 80% WG stand alone and an untreated control were carried on mango (*Mangifera indica*).

The below mentioned nine treatments including untreated control were evaluated with three replications:

TABLE 15

| Treatment | Compositions | Active ingredient (grams/ hectare) | Formulation Dosage in grams/ hectare | Mean % incidence of Powdery mildew(12th DAS) |
|---|---|---|---|---|
| 1 | Sulphur 15% + Thiophanate methyl 70% WDG | 300 + 1400 | 2000 | 8 |
| 2 | Sulphur 35% + Thiophanate methyl 50% WDG | 700 + 1000 | 2000 | 5 |
| 3 | Sulphur 40% + Thiophanate methyl 40% WDG | 800 + 800 | 2000 | 12 |
| 4 | Sulphur 60% + Thiophanate methyl 25% WDG | 1200 + 500 | 2000 | 7 |
| 5 | Sulphur 30% + Thiophanate methyl 35% SC | 600 + 700 | 2000 | 9 |
| 6 | Sulphur 7.5% + Thiophanate methyl 12.5% SC | 150 + 250 | 2000 | 14 |
| 7 | Sulphur 80% WG | 1250 | 1500 | 13 |
| 8 | Thiophanate methyl 70% WP | 800 | 1500 | 16 |
| 9 | Untreated control | — | — | 44 |

Sulphur+Thiophanate methyl compositions at various concentrations were evaluated for the disease controlling efficiency on Anthracnose and Powdery mildew. No toxicity was noted on the leaves, flowers or fruit for any of the chemicals tested.

All the combinations of Sulphur+Thiophanate methyl were sprayed at different phases/stages of mango cropping season.

The first spraying was conducted for the control of Powdery mildew at the flowering stage and it was found that treatments with Sulphur 35%+Thiophanate methyl 50% WDG at 700+1000 g.a.i per ha (Treatment 2) provided a highly effective control over the first powdery mildew infection reflecting a synergistic effect of Sulphur and Thiophanate methyl to manage the initial Powdery mildew infection. A very effective powdery mildew control for an extended period of 20 to 25 days was observed in the case of Treatment 2 and Treatment 4 further reflecting the synergy between Sulphur and Thiophanate methyl.

The above treatments with reduced dosages (e.g. Treatment 4) of the active ingredients were efficient in controlling the infestation as compared to the individual application of Thiophanate methyl and Sulphur at higher concentrations thereby signifying a synergistic effect of the Sulphur+Thiophanate methyl compositions.

In the case of SC formulations, the treatment with Sulphur 30%+Thiophanate methyl 35% SC at 600+700 g a.i. per ha (Treatment 5) was highly effective in controlling the Powdery mildew as compared to the individual treatments with Sulphur (Treatment 7) and Thiophanate methyl (Treatment 8).

It was also noted that the use of Sulphur and Thiophanate methyl compositions exhibited an improved foliage (darker greenish leaves) and the plants had an enhanced chlorophyll content, due to the presence of Sulphur in the composition.

Example 19

Bioefficacy of Sulphur Plus Trifloxystrobin

The experiment was conducted in the Nasik district of Maharashtra state in India with ten treatments and four replications.

The trials were conducted after sufficient growth of downy as well as powdery mildew fungus due to warm and humid weather conditions were observed on the vine/grape plants. Each treatment was carried out on two vine/grape infested plants and about 35% to 40% powdery mildew infestation was noted prior to the trials.

The treatments included combinations of Trifloxystrobin and Sulphur with varying concentrations of the active ingredients, Sulphur 80% WDG standalone, Trifloxystrobin 50% WG used as standards for comparison along with an untreated control.

The treatments carried out were as indicated in the table below:

TABLE 16

| Treatment | Composition | Active ingredient (grams/ hectare) | Formulation Dosage in grams/ hectare | Mean % incidence of powdery mildew | Yield (T/Ha) |
|---|---|---|---|---|---|
| 1 | Sulphur 50% + Trifloxystrobin2% WDG | 750 + 90 | 1500 | 12.38 | 20.6 |
| 2 | Sulphur 70% + Trifloxystrobin7% WDG | 1050 + 105 | 1500 | 1.78 | 23.0 |
| 3 | Sulphur 60% + Trifloxystrobin15% WDG | 900 + 900 | 1500 | 4.37 | 21.8 |
| 4 | Sulphur 50% + Trifloxystrobin20% WDG | 750 + 300 | 1500 | 6.48 | 21.2 |
| 5 | Sulphur 40% + Trifloxystrobin40% WDG | 600 + 600 | 1500 | 17.60 | 17.3 |
| 6 | Sulphur 40% + Trifloxystrobin20% SC | 600 + 300 | 1500 | 13.5 | 20.7 |

TABLE 16-continued

| Treatment | Composition | Active ingredient (grams/ hectare) | Formulation Dosage in grams/ hectare | Mean % incidence of powdery mildew | Yield (T/Ha) |
|---|---|---|---|---|---|
| 7 | Sulphur 20% + Trifloxystrobin 10% SC | 300 + 150 | 1500 | 20.38 | 19.9 |
| 8 | Sulphur 80% WDG | 1250 | 1500 | 18.44 | 18.3 |
| 9 | Trifloxystrobin 50% WG | 250 | 500 | 14.32 | 19.7 |
| 10 | Untreated control | — | | 42.39 | 14.2 |

It was observed that application of Sulphur 70%+Trifloxystrobin 7% WDG at 1050+105 g.a.i. per ha (Treatment 2) and Sulphur 60%+trifloxystrobin 15% WDG at 900+225 g a.i per ha (Treatment 3) proved highly effective in controlling the powdery mildew fungus effectively up to 20th DAS thereby reducing the conidial germination of *U. necator* and inhibiting the mycelial growth and sporulation of fungi. The above treatments showed strong curative action against the powdery mildew and hence the suppression of *U. necator* was demonstrated by the reduction of existing colonies when it was applied to mildewed leaves as compared to applications of Sulphur 80% WDG standalone (Treatment 8) and Trifloxystrobin 50% WG (Treatment 9) at higher concentrations of actives.

It was also observed that application of Sulphur 50%+Trifloxystrobin 20% WDG at 750+300 g.a.i. per ha (Treatment 4) and Sulphur 40%+Trifloxystrobin 40% WDG at 600+600 g a.i. per ha (Treatment 5) showed good control of the disease infestation up to the 15th DAS effectively.

In the case of SC compositions application of Sulphur 40%+trifloxystrobin 20% SC at 600+300 gm a.i per ha (Treatment 6) proved highly effective in controlling the powdery mildew spores and gave an enhanced control up to 15th DAS effectively in comparison with treatment of trifloxystrobin 50% WG used alone (Treatment 9)

The combination treatments of Sulphur and Trifloxystrobin provided a better control over the growth of powdery mildew fungus than trifloxystrobin and sulphur used alone at higher doses.

The inhibitory effectiveness of Sulphur+Trifloxystrobin makes it well suited for integration into control programs against powdery mildew diseases in vineyards, and as a component of resistance avoidance strategies. Apart from this, it was also noticed that the plants exhibited an improved foliage in the case of all the treatments with sulphur added to the composition in terms of increased greenness of the leaves, improved shine and a completely opened lamina of the leaf surface.

Example 20

Bioefficacy of Sulphur Plus Spiroxamine

The trials were carried out in the Nasik district of Maharashtra state in India with applications of Sulphur and Spiroxamine in a combination and also included individual applications of Sulphur as well as Spiroxamine as standards for comparison and an untreated control.

Seven treatments were experimented with four replications by keeping three vines for each treatment. Before the treatment, around 35% to 40% of the leaves were affected by the Powdery mildew incidence.

The treatments applied are as indicated in the table below:

TABLE 17

| Treatment | Compositions | Active ingredient (grams/ hectare) | Formulation Dosage in grams/ hectare | Mean % incidence of powdery mildew(7th DAS) | Yield (T/Ha) |
|---|---|---|---|---|---|
| 1 | Sulphur 40% + Spiroxamine 25% WP | 600 + 375 | 1500 | 12 | 20.5 |
| 2 | Sulphur 55% + Spiroxamine 35% WP | 825 + 525 | 1500 | 1 | 23.4 |
| 3 | Sulphur 80% + Spiroxamine 6% WP | 1200 + 90 | 1500 | 3 | 21.8 |
| 4 | Sulphur 30% + Spiroxamine 20% SE | 600 + 300 | 1500 | 4 | 17.4 |
| 5 | Sulphur 11% + Spiroxamine 6 SE. | 165 + 90 | 1500 | 18 | 13 |
| 5 | Control-Sulphur 80% WG | 1250 | 1500 | 18 | 16.3 |
| 7 | Control-Spiroxamine 50% EC | 150 | 300 | 16 | 18.7 |
| 8 | Untreated control | — | — | 32 | 14.5 |

After the 7th day of spraying, it was observed that the treatment Sulphur 55%+Spiroxamine 35% WP at 825+525 gm a.i per ha (Treatment 2) provided a highly effective control of the disease as the spores started drying and no further new spore formation was observed.

The treatments with Sulphur 40%+Spiroxamine 25% WP at 600+375 gm a.i per ha (Treatment 1) and Sulphur 30%+Spiroxamine 20% SE at 600+300 gm a.i per ha (Treatment 4) also gave an effective control as compared to the treatment with Spiroxamine 50% EC (Treatment 7) used alone.

In case of Sulphur 55%+Spiroxamine 35% WP at 825+525 gm a.i per ha (Treatment 2), sufficient control were observed up to 25th DAS, whereas the treatments 1, 3 and 4 were found effective up to 18th DAS. Treatment 5 was effective only up to 7DAS.

In the case of SE formulations it was observed that application of Sulphur 30%+Spiroxamine 20% SE at 600+300 gm a.i per ha (Treatment 4) provided an effective control over the disease.

In comparison the treatment of Spiroxamine 50% EC at a much higher concentration was found effective only up to the 12th DAS. The untreated control was found to be badly damaged by the severity of Powdery mildew incidence.

Example 21

Bioefficacy of Sulphur Plus Metrafenone

The trials were carried out in the Nasik district of Maharashtra state in India with applications of Sulphur and Metrafenone in a combination with varying concentration of active ingredients and also included standalone Sulphur 80% WDG and standalone Metrafenone 50% SC used as standards for comparison along with an untreated control.

The first few treatments are important and need to be applied at appropriate intervals, starting at bud break or early shoot growth. A powdery mildew index (PMI) model may be used to determine the appropriate treatment intervals as the frequency will depend upon weather conditions and choice of fungicide. Before the spray, 35% to 40% of the leaves were affected by the Powdery mildew incidence.

Eight treatments were experimented with four replications by keeping three vines for each treatment.

The treatments applied are as indicated in the table 18:

TABLE 18

| Treatments | Composition | Active ingredient (grams/hectare) | Formulation Dosage in grams/hectare | Mean % incidence of powdery mildew(10th DAS) | Yield (T/Ha) |
|---|---|---|---|---|---|
| 1 | Sulphur 70% + Metrafenone 10% WDG | 1050 + 150 | 1500 | 12.63 | 20.6 |
| 2 | Sulphur 60% + Metrafenone 20% WDG | 900 + 300 | 1500 | 7.58 | 21.6 |
| 3 | Sulphur 50% + Metrafenone 30% WDG | 750 + 450 | 1500 | 1.57 | 23.7 |
| 4 | Sulphur 35% + Metrafenone 15% SC | 525 + 225 | 1500 | 4.34 | 21.3 |
| 5 | Sulphur 25% + Metrafenone 5% SC | 375 + 75 | 1500 | 17.59 | 17.3 |
| 6 | Sulphur 80% WDG | 1250 | 1500 | 20.22 | 18.7 |
| 7 | Metrafenone 50% SC | 200 | 400 | 11.37 | 18.9 |
| 8 | Untreated control | — | — | 32.73 | 14.3 |

It was observed after the 10th day of spraying that the application of Sulphur 50%+Metrafenone 30% WDG at 750+450 g.a.i per ha (Treatment 3) in the form of water dispersible granules and Sulphur 35%+Metrafenone 15% SC at 525+225 g.a.i per hectare (Treatment 4) showed a highly effective control of the disease incidence as the spores started drying and no further new spores were observed. The control was observed up to the 18th to the 20th DAS, which reflected on the yield as well. These treatments were found to provide a good control as compared to the individual applications of Sulphur 80% WDG (Treatment 6) and Metrafenone 50% SC (Treatment 7)

It was further observed that the applications of Sulphur 70%+Metrafenone 10% WDG at 1050+150 g.a.i per ha (Treatment 1) and Sulphur 60%+Metrafenone 20% WDG at 900+300 g.a.i per ha (Treatment 2) were also found to be effective in controlling the infestation.

In the case of Sulphur 50%+Metrafenone 30% WDG at 750+450 g.a.i per ha (Treatment 3), increased control was observed up to the 25th DAS, whereas the other combination in WDG formulations were found effective up to the 18th DAS.

It was also observed in the case of SC formulations that application of Sulphur 35%+Metrafenone 15% SC at 525+225 g.a.i per ha (Treatment 4) showed a sufficient control of the disease infestation despite being used at very low dosages of the individual active ingredients as compared to the Treatment 6 and Treatment 7.

The untreated control was badly damaged by the severity of Powdery mildew incidence.

Example 22

Bioefficacy of Sulphur Plus Cymoxanil

The trials were conducted in the state of West Bengal in India. The first few treatments are important and should be applied at appropriate intervals, starting at bud break or early shoot growth. A late blight index (PMI) model may be used to determine appropriate treatment intervals because frequency will depend upon weather conditions and choice of fungicide.

Before treatment, a sufficient incidence of around 20-25% of leaves affected by the late blight was observed. Seven treatments were experimented with four replications by keeping three vines for each treatment.

The treatments are as indicated in the table below:

TABLE 19

| Treatment | Compositions | Active ingredient (grams/hectare) | Formulation Dosage in grams/hectare | Mean % incidence of late blight after 7th DAS | Yield (T/Ha) |
|---|---|---|---|---|---|
| 1 | Sulphur 50% + cymoxanil 30% WDG | 750 + 450 | 1500 | 8.4 | 20.3 |
| 2 | Sulphur 60% + cymoxanil 20% WDG | 900 + 300 | 1500 | 2.0 | 23.7 |
| 3 | Sulphur 70% + cymoxanil 15% WDG | 1050 + 225 | 1500 | 4.7 | 21.3 |
| 4 | Sulphur 35% + cymoxanil 10% SC | 525 + 150 | 1500 | 3.3 | 20.5 |
| 5 | Sulphur 25 + cymoxanil 7.5% SC | 375 + 112.5 | 1500 | 14.6 | 17.6 |
| 6 | Sulphur 80% WG | 1250 | 1500 | 18.4 | 17.3 |
| 7 | Cymoxanil 50% WP | 300 | 600 | 16.8 | 18.5 |
| 8 | Untreated control | — | — | 32.5 | 13.6 |

It was observed that after the 5th day of spraying, that the application of Sulphur 60%+cymoxanil 20% WDG at 900+300 g.a.i per ha (Treatment 2) showed a highly effective control as the spores started drying and a very less number of spores were observed on the 5th day after spraying. No spores or new sporulation were observed on the 7th day after spraying. The composition was effective despite being used at very low dosages of the individual active ingredients.

The treatments with Sulphur 70%+Cymoxanil 15% WDG at 1050+225 g.a.i per ha (Treatment 3) and Sulphur 50%+Cymoxanil 30% WDG at 750+450 g.a.i. per ha (Treatment 1) and Sulphur 35%+Cymoxanil 10% SC at 525+150 g.a.i per ha (Treatment 4) also gave a good control as compared to the individual treatment of the actives (Treatments 6 and 7)

In the case of application of Sulphur 60%+Cymoxanil 20% WDG at 900+300 g.a.i per ha (Treatment 2), an increased control was observed up to the 20th DAS, whereas in the case of Treatments 1 and 3 good control was observed up to the 15th DAS.

The treatment with Sulphur 35%+Cymoxanil 10% SC at 525+150 g.a.i per ha (Treatment 4) was found effective up to the 12th DAS with much better control over the late blight incidence and proved better with the final yield of potato at 20.5 MT per hectare as compared to the individual treatment of the actives (Treatments 6 and 7)

The untreated control was badly damaged by the severity of late blight incidence.

From the foregoing it will be observed that numerous modifications and variations can be effectuated without departing from the true spirit and scope of the novel concepts of the present invention. It is to be understood that no limitation with respect to the specific embodiments illustrated is intended or should be inferred.

I claim:

1. A pesticidal composition consisting of (a) sulphur in the range of 25% to 80% w/w of the total composition; (b) azoxystrobin in the range of 3% to 20% w/w of the total composition; and (c) agrochemically acceptable excipients.

2. A pesticidal composition consisting of (a) sulphur in the range of 20% to 70% w/w of the total composition; (b) trifloxystrobin in the range of 1% to 40% w/w of the total composition; and (c) agrochemically acceptable excipients.

3. A pesticidal composition consisting of (a) sulphur in the range of 7.5% to 60% w/w of the total composition; (b) thiophanate methyl in the range of 12.5% to 70% w/w of the total composition; and (c) agrochemically acceptable excipients.

4. A pesticidal composition consisting of (a) sulphur in the range of 25% to 70% w/w of the total composition; (b) chlorothalonil in the range of 7.5% to 50% w/w of the total weight of the composition; and (c) agrochemically acceptable excipients.

5. A pesticidal composition consisting of (a) sulphur in the range of 17.5% to 55% w/w of the total composition; (b) iprodione in the range of 15% to 60% w/w of the total weight of the composition; and (c) agrochemically acceptable excipients.

6. A pesticidal composition consisting of (a) sulphur in the range of 20% to 70% w/w of the total composition; (b) prochloraz in the range of 12.5% to 60% w/w of the total weight of the composition; and (c) agrochemically acceptable excipients.

7. A synergistic pesticidal composition consisting of
(a) sulphur in the range of 11% to 80% w/w of the total composition;
(b) a fungicide or a salt thereof selected from the group consisting of fenhexamid in the range of 12.5% to 45% w/w of the total composition, fenamidone in the range of 3% to 20% w/w of the total composition, cyazofamid in the range of 2.25% to 40% w/w of the total composition, pyraclostrobin in the range of 3.5% to 15% w/w of the total composition, validamycin in the range of 1.5% to 10% w/w of the total composition, kasugamycin in the range of 1.5% to 10% w/w of the total composition, cyprodinil in the range of 5% to 30% w/w of the total composition, pencycuron in the range of 5% to 30% w/w of the total composition, hexaconazole in the range of 1.5% to 8% w/w of the total composition, epoxiconazole in the range of 1.5% to 20% w/w of the total composition, prothioconazole in the range of 5% to 60% w/w of the total composition, and spiroxamine in the range of 6% to 35% w/w of the total composition; and
(c) agrochemically acceptable excipients;
wherein said synergistic pesiticidal composition exhibits superior pesticidal efficacy compared with a composition that uses either sulphur or fungicide.

8. The synergistic pesticidal composition of claim 7, wherein the composition is in a liquid form or a solid form.

9. The synergistic pesticidal composition of claim 7, wherein the composition is in a form selected from the group consisting of water dispersible granules, suspension concentrates, wettable powders, emulsifiable concentrates, seed dressing, gels, suspo emulsions, capsulated suspensions, emulsions in water, and oil dispersions.

10. The synergistic pesticidal composition of claim 7, consisting of (a) sulphur in the range of 17.5% to 55% w/w of the total composition; (b) fenhexamid in the range of 12.5% to 45% w/w of the total weight of the composition; and (c) agrochemically acceptable excipients.

11. A synergistic pesticidal composition consisting of:
(a) sulphur in the range of 11% to 80% w/w of the total composition;
(b) a fungicide or a salt thereof selected from the group consisting of fenhexamid in the range of 12.5% to 45% w/w of the total composition, fenamidone in the range of 3% to 20% w/w of the total composition, cyazofamid in the range of 2.25% to 40% w/w of the total composition, pyraclostrobin in the range of 3.5% to 15% w/w of the total composition, validamycin in the range of 1.5% to 10% w/w of the total composition, kasugamycin in the range of 1.5% to 10% w/w of the total composition, cyprodinil in the range of 5% to 30% w/w of the total composition, pencycuron in the range of 5% to 30% w/w of the total composition, hexaconazole in the range of 1.5% to 8% w/w of the total composition, epoxiconazole in the range of 1.5% to 20% w/w of the total composition, prothioconazole in the range of 5% to 60% w/w of the total composition, and spiroxamine in the range of 6% to 35% w/w of the total composition; and
(c) agrochemically acceptable excipients;
wherein said pesticidal composition exhibits superior fungal control and enhanced yield at lower dosages of sulphur and the fungicide compared with individual sulphur or individual fungicide.

* * * * *